(12) United States Patent
Cormier et al.

(10) Patent No.: US 8,854,451 B2
(45) Date of Patent: Oct. 7, 2014

(54) AUTOMATED BUBBLE DETECTION APPARATUS AND METHOD

(75) Inventors: Josh Cormier, Los Gatos, CA (US); Fangli Hao, Cupertino, CA (US); Hong Shih, Walnut, CA (US); Tuochuan Huang, Saratoga, CA (US); John Daugherty, Fremont, CA (US); Allan Ronne, Santa Clara, CA (US); Fred Dennis Egley, Sunnyvale, CA (US)

(73) Assignee: Lam Research Corporation, Fremont, CA (US)

( * ) Notice: Subject to any disclaimer, the term of this patent is extended or adjusted under 35 U.S.C. 154(b) by 392 days.

(21) Appl. No.: 13/276,837

(22) Filed: Oct. 19, 2011

(65) Prior Publication Data

US 2013/0100278 A1    Apr. 25, 2013

(51) Int. Cl.
*H04N 7/18*        (2006.01)
*G01N 21/27*       (2006.01)
*G01N 17/02*       (2006.01)
*C25D 11/04*       (2006.01)

(52) U.S. Cl.
CPC ............. *G01N 17/02* (2013.01); *G01N 21/272* (2013.01); *C25D 11/04* (2013.01); *G06T 2200/28* (2013.01)
USPC ........ 348/92; 348/E7.085; 348/127; 148/518; 205/328; 427/453; 382/103; 382/203

(58) Field of Classification Search
CPC ...... G01N 21/00; G01N 21/031; G01N 21/13
USPC ................................. 348/86, 91, 92
See application file for complete search history.

(56) References Cited

U.S. PATENT DOCUMENTS

| | | | |
|---|---|---|---|
| 5,607,623 A | 3/1997 | Benton et al. | |
| 6,620,338 B2 | 9/2003 | Fan et al. | |
| 6,622,542 B2 | 9/2003 | Derek et al. | |
| 6,726,774 B2 | 4/2004 | Tzeng et al. | |
| 6,843,099 B2 | 1/2005 | Derek et al. | |
| 7,048,814 B2 * | 5/2006 | Lin et al. ................. | 148/518 |
| 7,231,805 B2 | 6/2007 | Bretmersky | |
| 7,829,468 B2 | 11/2010 | Keil et al. | |
| 8,033,164 B2 | 10/2011 | Dermody et al. | |
| 8,614,739 B2 * | 12/2013 | Pollack et al. ............ | 348/84 |
| 2003/0134134 A1 * | 7/2003 | Simpson et al. .......... | 428/469 |
| 2004/0024296 A1 | 2/2004 | Krotkov et al. | |

(Continued)

OTHER PUBLICATIONS

C. Ribbing, 'Improved contrast in confocal microscopy by using a blue frequency doubled diode-pumped solid-state laser', 2003, Optical of America, p. 1-2.*

*Primary Examiner* — Sath V Perungavoor
*Assistant Examiner* — Dakshesh Parikh
(74) *Attorney, Agent, or Firm* — Buchanan Ingersoll & Rooney PC (57) ABSTRACT

An automated hydrogen bubble detection apparatus includes a horizontal support surface on which a test coupon can be supported, a transparent tube having an open top and an open bottom and operable to contain a test solution when positioned on a test coupon, a camera arranged to view a test solution in the transparent tube, and a controller in communication with the camera and effective to operate the camera such that at least one video segment is recorded by the camera and analyzed to detect first bubble and continuous bubble generation. A method of evaluating corrosion resistance of coatings on aluminum and steel in acidic solution is also included.

14 Claims, 12 Drawing Sheets

(56) References Cited

U.S. PATENT DOCUMENTS

| | | | |
|---|---|---|---|
| 2006/0197664 A1* | 9/2006 | Zhang et al. | 340/555 |
| 2007/0222973 A1* | 9/2007 | Hoshiko et al. | 356/39 |
| 2008/0166037 A1* | 7/2008 | Mandrachia et al. | 382/133 |
| 2008/0241517 A1 | 10/2008 | Kenworthy et al. | |
| 2009/0133480 A1* | 5/2009 | Ivanov et al. | 73/64.51 |
| 2009/0155476 A1* | 6/2009 | Francis et al. | 427/421.1 |
| 2009/0214825 A1 | 8/2009 | Sun et al. | |
| 2011/0013012 A1* | 1/2011 | Hummel et al. | 348/81 |

* cited by examiner

AUTOMATED BUBBLE DETECTION APPARATUS AND METHOD

BACKGROUND

Aluminum alloys have been widely used in semiconductor plasma etching tools over the past thirty years. For example, anodized aluminum has unique properties such as high corrosion resistance, high surface micro-hardness, high plasma resistance, low cost, and large manufacture capabilities when compared to bare aluminum.

However, poor anodization and/or coating leads to a short lifetime, severe corrosion, high particles and defects, and high metal contamination of plasma etched wafers. To test the corrosion resistance of such parts, bubble testing, such as HCl bubble testing can be used. Commonly assigned U.S. Patent Application Publication 2008/0241517 discloses details of HCl bubble testing. When anodization fails, HCl and/or other acids react with aluminum and/or steel to generate hydrogen bubbles. Thus, the appearance of hydrogen bubbles can be used to determine the time of failure or the bubble time. However, the bubble test can be somewhat limited since human monitoring is required for the duration of the test.

Thus, an automated bubble detection apparatus, which requires minimal human intervention, is repeatable and cost effective is desirable.

SUMMARY

An automated hydrogen bubble detection apparatus and method are disclosed herein. In a preferred embodiment, the automated hydrogen bubble detection apparatus comprises a horizontal support surface on which a test coupon can be supported, a transparent tube having an open top and an open bottom and operable to contain an acidic test solution when positioned on a test coupon, a camera arranged to view a test solution in the transparent tube and record images of the acidic test solution above the test coupon, and a controller in communication with the camera and effective to analyze video segments recorded by the camera and identify presence of bubbles in the acidic test solution.

Preferably, the apparatus also includes at least one light. In the preferred embodiment, the transparent tube can be positioned between the light and the camera. Preferably, the light is a blue LED light.

In the preferred embodiment, the automated bubble detection apparatus includes two or more transparent tubes. Also preferably, the camera is supported on a movable carriage which positions the camera in front of each transparent tube at predetermined intervals ranging from about three minutes to about five minutes. Moreover, the camera records video segments for up to about 48 hours.

Preferably, the tube is a quartz tube, a glass tube or a poly-glass tube, and the test solution comprises a 2 wt. % to a 5 wt. % HCl solution, a 2 wt. % to a 5 wt. % $HNO_3$ solution or a 2 wt. % to a 5 wt. % $H_2SO_4$ solution.

In the preferred embodiment, the automated hydrogen bubble detection apparatus also comprises at least two horizontal support surfaces arranged side by side or spaced vertically apart. A plurality of test coupons are supported on the horizontal support surfaces. Preferably, the camera is mounted on a movable carriage which sequentially positions the camera adjacent each of the transparent tubes.

In another embodiment, the horizontal support surface is a disk-shaped surface on which multiple test coupons can be supported. Preferably, the disk-shaped surface can be rotated around the camera. Alternatively, the camera can be mounted on a moveable carriage which rotates the camera so as to sequentially position the camera adjacent each transparent tube mounted on the disk-shaped surface.

In the preferred embodiment, the camera is positioned about 8 inches to about 12 inches from the transparent tube. More preferably, the camera is positioned about 10 inches from the transparent tube. Also preferably, the camera is a monochrome camera and dark-field detection is used to locate bubbles in the video segments generated by the camera. Moreover, the camera has a resolution of at least about 1240× 1080 pixels and a frame rate of at least about 35 frames per second (fps).

Also preferably, the transparent tube is sealed to an upper surface of a test coupon by an O-ring. Moreover, the controller comprises a computer, which uploads video segments from the camera and runs an algorithm to detect hydrogen bubbles on each video segment and the time and date thereof. Preferably each video segment is converted to a black and white image.

In a preferred embodiment, the method of detecting corrosion resistance of coatings on aluminum or steel by an acidic test solution includes mounting a transparent tube having an open top and an open bottom on a test coupon such that an open bottom of the tube is sealed to an exposed surface of the test coupon, placing a quantity of an acidic test solution in the transparent tube such that the acidic test solution contacts a surface of the test coupon, positioning a camera adjacent the transparent tube such that the acidic test solution is in the field of view of the camera, recording video segments of the acidic test solution in the transparent tube over a period of time, uploading the video segments from the camera to a controller and analyzing the video segments uploaded to the controller to determine first bubbles generation and steady state generation of bubbles in the acidic test solution.

In the preferred embodiment, the method includes mounting at least two transparent tubes on at least two test coupons. In this embodiment, the method also includes positioning each of the transparent tubes adjacent the camera every three to five minutes. Alternatively, the method can include mounting the camera on a movable carriage, which moves and sequentially positions the camera adjacent each transparent tube at a predetermined interval.

Preferably, the camera is positioned adjacent each of the transparent tubes every three to five minutes so as to record time lapsed video segments of each transparent tube. Also preferably, the camera periodically records video segments of the tubes for up to about 48 hours.

Preferably, the controller is a computer. In the preferred embodiment, the test solution is a solution containing HCl and the controller and camera cooperate to detect the first hydrogen bubbles suspended in the HCl solution. The computer analyzes images taken by the camera to identify hydrogen bubbles not more than about 2 seconds apart and records the date and time of detection of the first hydrogen bubbles. Also preferably, the controller and camera cooperate to detect the steady state bubble generation in which about 30% of the image area is covered by hydrogen bubbles and wherein the controller records the date and time of the detection of the steady state bubble generation.

In the preferred embodiment, the analyzing includes running a detection algorithm against the video segments to detect the first hydrogen bubbles and the steady state. Preferably, the analyzing also includes converting each video segment to a binary image and locating clusters of bubbles in each video segment. The method can also include generating a report based on the analysis of the video segments. The report can include date and time of first bubbles and steady state for each test coupon.

DETAILED DESCRIPTION

Components of semiconductor processing equipment can be made of anodized aluminum or coated metal parts of aluminum or steel. To evaluate corrosion resistance of the anodized outer layer or coating, it is conventional to carry out an acid corrosion test. This test can be used to evaluate corrosion resistance of plasma chamber components exposed to corrosive gases and/or plasma erosion wherein the productivity, defect and particle performance, as well as metal contamination rely on the quality of anodization and surface coatings on aluminum and/or steel. High corrosion resistant coatings on steel and/or aluminum can provide much better productivity performance for plasma etch tools.

Poor anodization and/or coating can lead to a short lifetime, severe corrosion, high particles and defects, and high metal contamination of plasma processed wafers.

The quality of anodized aluminum depends on many factors including raw aluminum alloys used (e.g., thin plate, forged, casted, extruded alloys, thick block alloys through rolling and forging et al., different types of alloys such as 6XXX, 5XXX, 2XXX and 7XXX series of aluminum alloys), surface condition of aluminum alloys before anodization (e.g., machined, polished, and bead-blasted), different anodization processes (e.g., Type II, Type III, oxalic, and mixed acid anodization), and post treatment after anodization.

Bubble testing can be used to determine the overall acidic corrosion resistance of anodized aluminum and other surface coatings. To perform a bubble test, epoxy can be used to mount a transparent poly-glass, glass or quartz tube on at least a portion of the surface of a test coupon. Preferably, the tube is at least partially open at the top thereof to allow for venting and/or placing of the test solution in the tube once mounted on the test coupon. After drying, a 5 wt. % HCl solution or other test solution is poured into the tube, and the coated surface is observed for the first appearance of $H_2$ bubbles and continuous $H_2$ bubble generation from the coated surface. In the bubble test, when the anodization fails, HCl directly reacts with aluminum to generate $H_2$ bubbles. The time until first bubbles and steady state when continuous $H_2$ bubble generation are observed is determined by automated image detection of the appearance of bubbles as disclosed herein.

As used herein, the term "steady state" describes the generation of continuous $H_2$ bubbles which is evidenced by having about 30% of an image area covered by the $H_2$ bubbles.

As used herein, the term "first bubbles" describes the point at which bubbles are observed in the test solution and continue not more than about 2 seconds apart.

As used herein, the term "test solution" describes acidic solutions selected from the group consisting of a 2 wt. % to a 5 wt. % HCl solution, a 2 wt. % to a 5 wt. % $HNO_3$ solution or a 2 wt. % to a 5 wt. % $H_2SO_4$ solution.

Preferably, the test solution does not include HF solutions because such solutions attack the silicon and magnesium in anodized layers and thus would not be a reliable method of determining whether the acid penetrates the coating and attacks the underlying metal.

The corrosion resistance of the porous layer of anodized aluminum can play a critical role in the overall corrosion resistance in acid because of its thickness. For example, any anodized aluminum without post treatment such as hot DIW seal or steam seal only has a HCl bubble time between about 2 minutes and about 20 minutes because the porous layer is widely open to penetration by the HCl acid.

Based on the impact of the above factors, there are large variations of performance of anodized aluminum in acidic solutions such as a 5 wt. % HCl solution. Some anodized aluminum samples or components showed no corrosion in 5 wt. % acid after being immersed for 24 hours, while some showed corrosion within 5 minutes. Thus, the bubble test is a good indication of the integrity of the anodized layer.

The chemical reaction during acidic corrosion when testing using a 5 wt. % HCl solution is shown in Examples 1 and 2.

Example 1

Anodized aluminum corrosion by 5 wt % HCl solution at room temperature:

6HCl+2Al(through micro-cracks and defects on anodized layer)=2AlCl$_3$+3H$_2$(hydrogen bubbles)

2AlCl$_3$+3H$_2$O=2Al(OH)$_3$+6HCl

6HCl+2Al(through micro-cracks and defects on anodized layer)=2AlCl$_3$+3H$_2$(hydrogen bubbles).

Example 2

Anodized aluminum corrosion exposed to Cl$_2$/BCl$_3$ plasma after exposure to atmosphere:

2Al(micro-cracks and defects on anodized aluminum)+3Cl$_2$=2AlCl$_3$(pitting corrosion)

2AlCl$_3$+3H$_2$O(moisture)=2Al(OH)$_3$+6HCl

6HCl+2Al(through micro-cracks and defects on anodized layer)=2AlCl$_3$+3H$_2$(pitting corrosion).

Figure 3A:
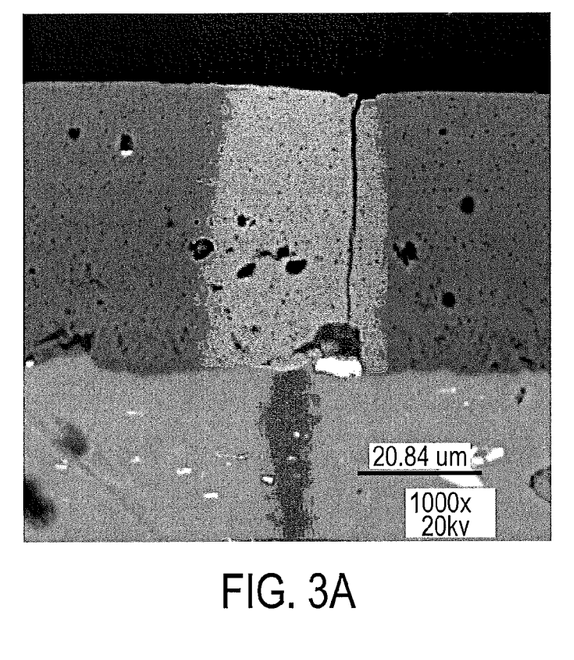
FIGS. 3A and 3B are scanning electron microscope (SEM) cross section video segments showing the vertical microcracks along anodized aluminum for sample having an HCl bubble time of between 10 and 20 minutes.
Figure 3B:
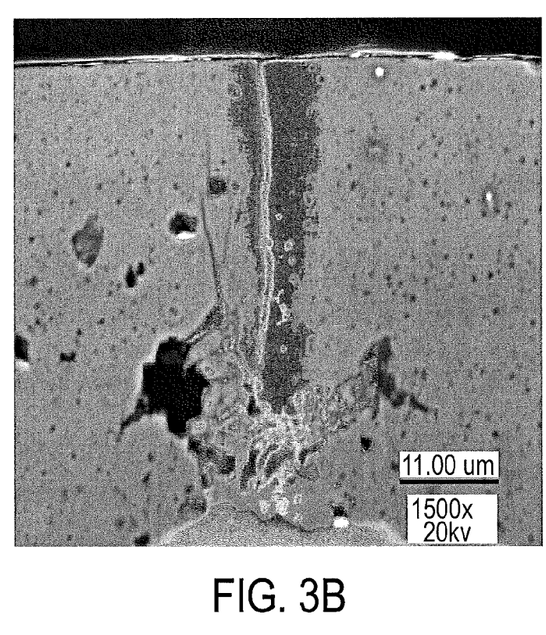
Figure 4:
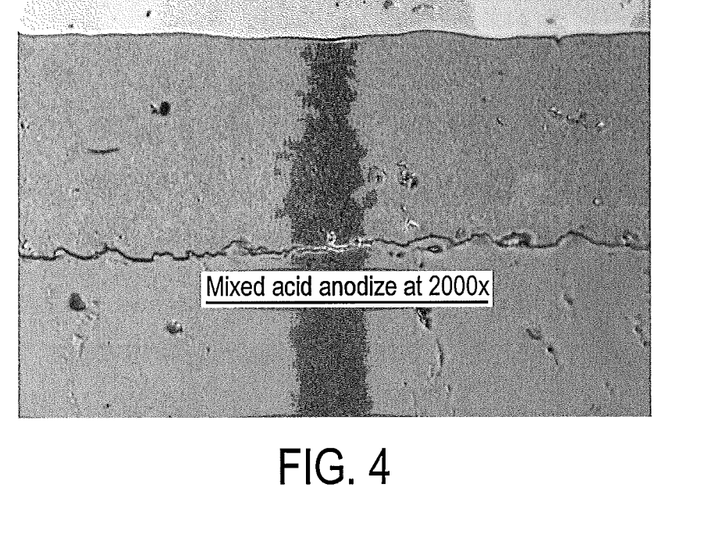
FIG. 4 is a SEM cross section analysis showing no microcracks and very low defects for a sample having an HCl bubble time of longer than 24 hours.
Figure 5A:
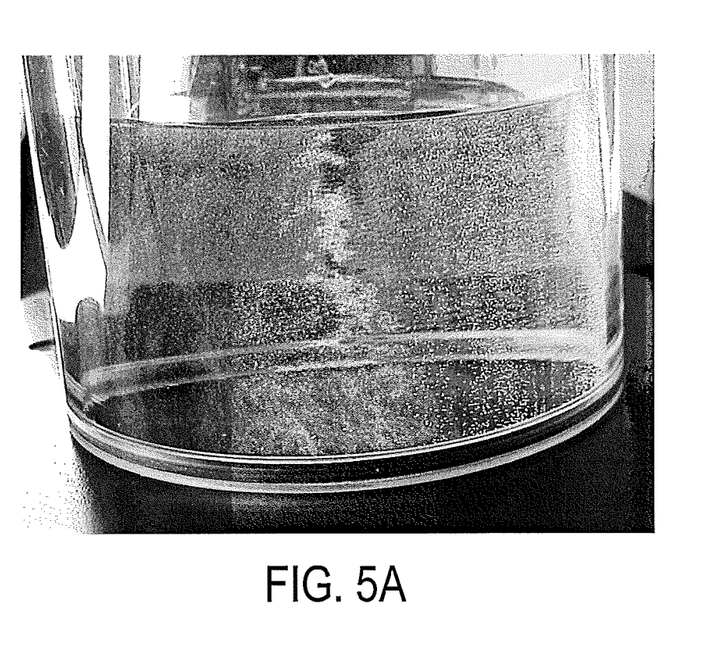
FIG. 5A is a photograph showing hydrogen generated during a first HCl bubble test on anodized aluminum.
Figure 5B:
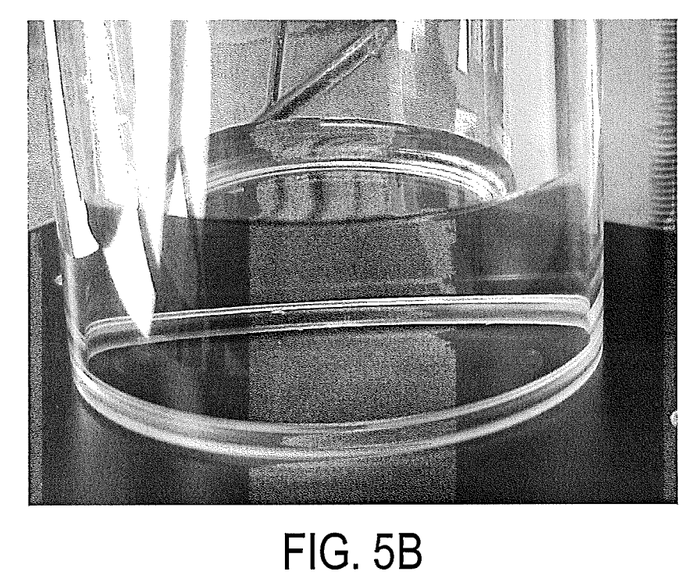
FIG. 5B is a photograph showing no corrosion occurred on anodized aluminum during a second HCl bubble test on anodized aluminum.

FIGS. 3-5 demonstrate the results of the chemical reaction and testing as described in Example 1. The SEM cross section photographs shown in FIGS. 3A and 3B show vertical micro-cracks along anodized aluminum after between 10 and 20 minutes exposure to 5 wt. % HCl solution. FIG. 4 is a SEM cross section photograph showing no micro-cracks and very low defects for a sample having an HCl bubble time of longer than 24 hours. FIG. 5A shows hydrogen bubbles generated during a first HCl bubble test on anodized aluminum. FIG. 5B shows no corrosion occurred on anodized aluminum during a second HCl bubble test on anodized aluminum.

Figure 1:
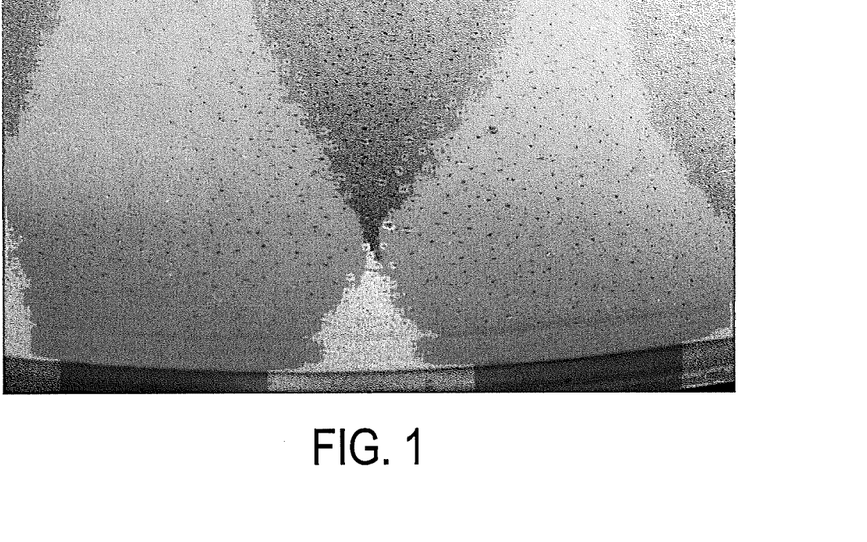
FIG. 1 is a photograph showing pitting corrosion on anodized aluminum observed under $Cl_2/BCl_3$ plasma.
Figure 2:
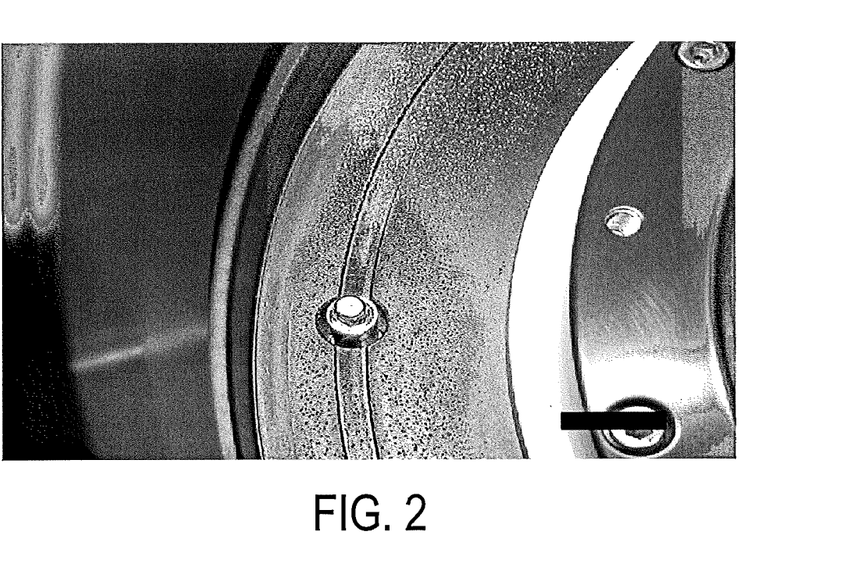
FIG. 2 is a photograph showing severe pitting corrosion of anodized aluminum observed under $Cl_2/BCl_3$ plasma.

FIGS. 1 and 2 are photographs showing the results of the chemical reaction, as described in Example 2, resulting from plasma erosion during use in semiconductor etching with Cl$_2$/BCl$_3$ plasma.

Since the acidic corrosion resistance of anodized aluminum is determined by the continuous generation of hydrogen bubbles when the acid reacts with bare aluminum through defects and micro-cracks on anodic layers, the onset of bubble generation during bubble testing can run from a few minutes to 24 hours or more. Because of the large time differences in bubble generation during bubble tests, it can be very difficult to perform the bubble test because human monitoring is required for the duration of the test. An automated detection apparatus for recording the hydrogen bubbles during the bubble test would be desirable to overcome these difficulties.

As used herein, the term "test coupon" describes a solid material having a surface coating. The test coupon can comprise anodized aluminum and/or other surface coatings on bare aluminum and can be a small section of material or a part such as a component of a plasma reactor. Alternatively, the test coupon can be a portion of a semiconductor plasma etching tool. The test coupon can include the following materials: anodized aluminum alloys (2XXX, 5XXX, 6XXX, 7XXX, casting aluminum alloys, and aluminum metal matrix composite materials et al), electroless Ni and Co coatings on aluminum alloys and on steel, thermal spray coatings such as Al$_2$O$_3$, ZrO$_2$, B$_4$C, and CeO$_2$ coatings on aluminum or on anodized aluminum, CVD and PVD coatings on steel and on aluminum alloys, polymer and organic coatings on aluminum alloys, anodized aluminum alloys, and on steel, other surface coatings and surface modification coatings such as chromate conversion coatings, surface modification layer through rare earth components, or other surface coatings on aluminum alloys and on steel.

As used herein, the term "video segments" describes single frame images and/or multi-frame video clips.

Figure 6:
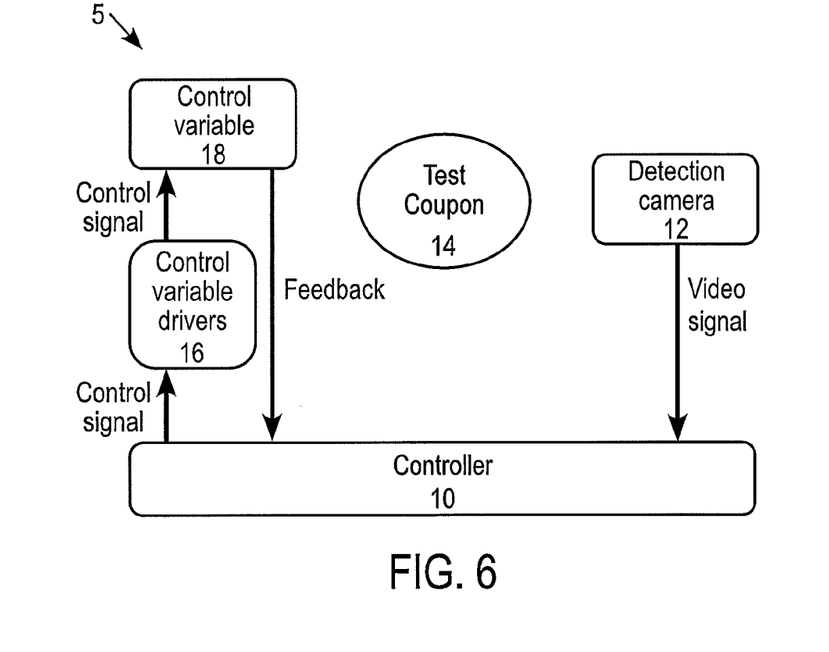
FIG. 6 is a schematic illustrating a preferred embodiment of the automated bubble detection apparatus as described herein.

As shown in FIG. 6, the automated bubble detection apparatus 5 of the preferred embodiment generally includes a controller 10, which can comprise a computer. The controller 10 communicates with a detection camera 12, which records video segments of the test solution over a test coupon 14 during bubble testing. The video segments can then be uploaded from the camera 12 to the controller 10 for analysis. The controller 10 provides a control signal to control variable drivers 16, which in turn provide a control signal to control variables 18. The control variables 18 provide feedback to the main controller 10. The control variables 18 comprise time per sample, threshold number used to create a binary image of the video segments, and other such factors which can be altered to adjust the measured test conditions.

Figure 7:
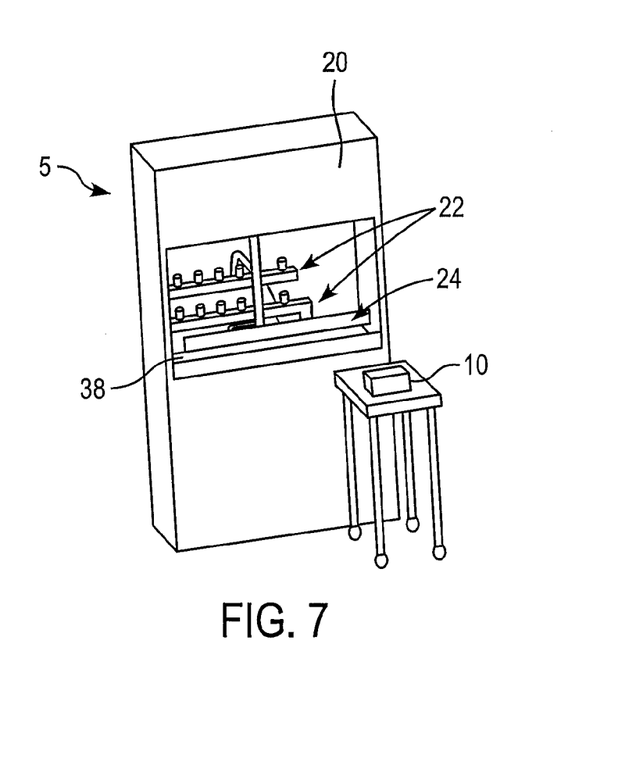
FIG. 7 is a perspective view of one embodiment of an automated bubble detection apparatus as disclosed herein.
Figure 8:
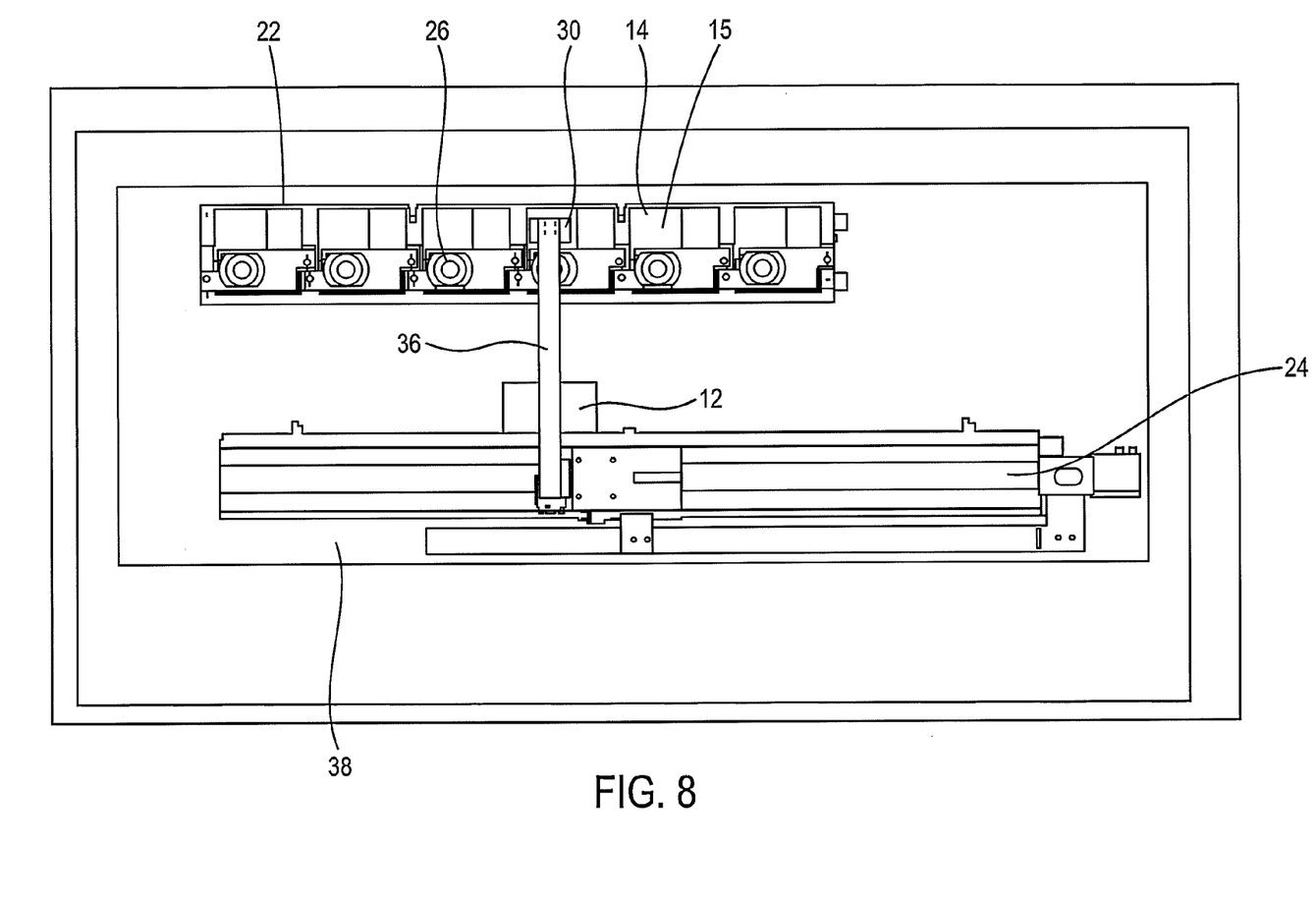
FIG. 8 is a top view of the automated bubble detection apparatus of FIG. 7.

In the preferred embodiment, as shown in FIGS. 7 and 8, the automated bubble detection apparatus 5 includes a test coupon 14 comprising a surface coating 17 on aluminum and/or steel 19 (shown in FIG. 15) and a transparent tube 26 containing a test solution and mounted with one open end of the tube on a surface 15 of the test coupon 14 such that the test solution in the tube contacts the surface 15. Preferably, the test solution is a 5 wt. % HCl solution, a 2 wt. % to a 5 wt. % HNO$_3$ solution or a 2 wt. % to a 5 wt. % H$_2$SO$_4$ solution.

In the preferred embodiment, the camera 12 is positioned adjacent the tube 26 for a predetermined period of time, and is focused so as to record video segments of the test solution contained therein during testing. Preferably, the controller 10 is in communication with the camera 12 before, during and/or after the test. Also preferably, the camera records video segments with date and time stamps during the bubble test and uploads the video segments to the controller 10. In another embodiment, the uploading can occur concurrently with recording of the video segments and the controller can record data including the time and date as the images upload. Alternatively, the video segments can be uploaded after a set period of time, for example, 48 hours, and the date and time stamps of the video segments can also be uploaded and used to analyze the video segments.

Once uploaded, the video segments are analyzed to detect both the first bubbles and the steady state bubbles and the time of occurrence of each event. A report can then be generated, which details the date, time of first bubbles and time of steady state bubbles for each test coupon included in the bubble test. The report can be used to determine the corrosion resistance of the test coupon. Alternatively, the report can be used to identify a window of time when such bubbles occur so that human monitoring can also be conducted.

Preferably, the camera 12 is a monochrome camera having a resolution of at least about 1240×1080 pixels and a frame rate of at least about 35 frames per second (fps). For example, the camera can be an EO GigE CMOS Machine Vision Camera having a TECHSPEC® Focusable Double Gauss Macro Imaging Lens both available from Edmund Optics of Barrington, N.J. Preferably, the camera 12 is positioned such that the liquid in the tube 26 fills up as much of the image frame as possible. Preferably, the width of the field of view is about 1 inch and the depth of the field of view is about 2 inches. Also preferably, dark field detection is used to locate bubbles within the tube. Thus, each H$_2$ bubble shows up as a dark area against a white background. Typically, the smallest H$_2$ bubbles are about 50 micrometers in diameter.

In a testing apparatus wherein a plurality of test coupons, such as 2 to 30 or more, are arranged for viewing by the camera, the camera 12 is mounted on a movable carriage 24 which can position the camera adjacent each transparent tube to capture an image of the test solution in the tube. Preferably, the carriage 24 is capable of moving in both the x-axis and the y-axis so as to position the camera 12 adjacent each test coupon 14 housed on a support surface 22. In other embodiments, the carriage 24 can be designed to move diagonally or may rotate as needed depending upon the arrangement of the test coupons.

Preferably, when in position, the camera 12 is about 8 inches to about 12 inches from the outer surface of the tube 26. For example, in a preferred embodiment, the camera 12 is about 10 inches from the outer surface of the tube 26.

As shown in FIG. 8, the carriage 24 can also include a mounting clamp 36 for mounting a light 30. Preferably, the light 30 and camera 12 are arranged such that the tube 26 is located between the light 30 and camera 12. In the preferred embodiment, the light 30 is a blue LED backlight, which provides the most visible light to the camera 12, and helps provide necessary contrast to detect and record video segments of the bubbles within the tube 26. Moreover, the carriage 24 can be moveably attached to a fixed base 38, which can be a table, desk, support surface, floor or other suitable support structure.

Preferably, each test coupon 14 is held on a horizontal support surface 22. In one embodiment, the horizontal support surface 22 is in the form of at least one linear support surface. Also preferably, the support surface 22 can be housed in a ventilation cabinet 20, which vents gases produced during the bubble test.

In the preferred embodiment, the apparatus 5 includes multiple horizontal support surfaces 22 holding one or more test coupons 14. For example, the apparatus 5 can include two support surfaces 22 each holding twelve horizontal test coupons 14 with tubes 26 mounted vertically on each test coupon 14. The horizontal support surfaces 22 can be arranged in a bookshelf configuration as shown in FIGS. 7 and 8. Preferably, the carriage 24 moves and positions the camera 12 and light 30 every 7 to 10 seconds so that the camera 12 records one or more video segments of the test solution in the tube 26 on each test coupon 14 every 3 to 5 minutes. Also preferably, the controller 10 can include a memory which can be programmed to include 24 sub-folders and the video segments can be uploaded to the corresponding sub-folder for analysis.

In the preferred embodiment, the analysis of the video segments is performed while the bubble test is ongoing. Thus, once each sample hits steady state bubble generation, recording of the bubble test can be stopped. In other embodiments, the analysis of the video images can be conducted periodically during the bubble test or after the bubble test has run for a set period of time, for example 48 hours.

Figure 9:
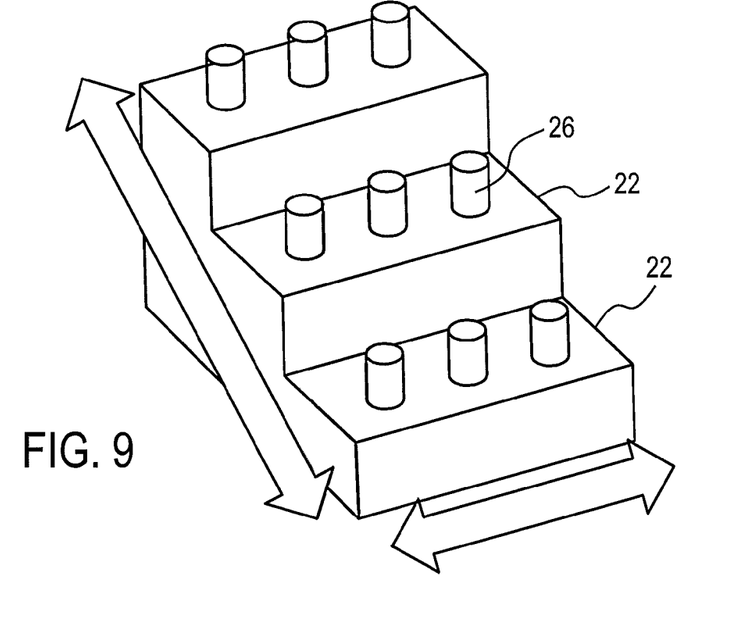
FIG. 9 is an illustration of a second embodiment of an arrangement of support surfaces.
Figure 10:
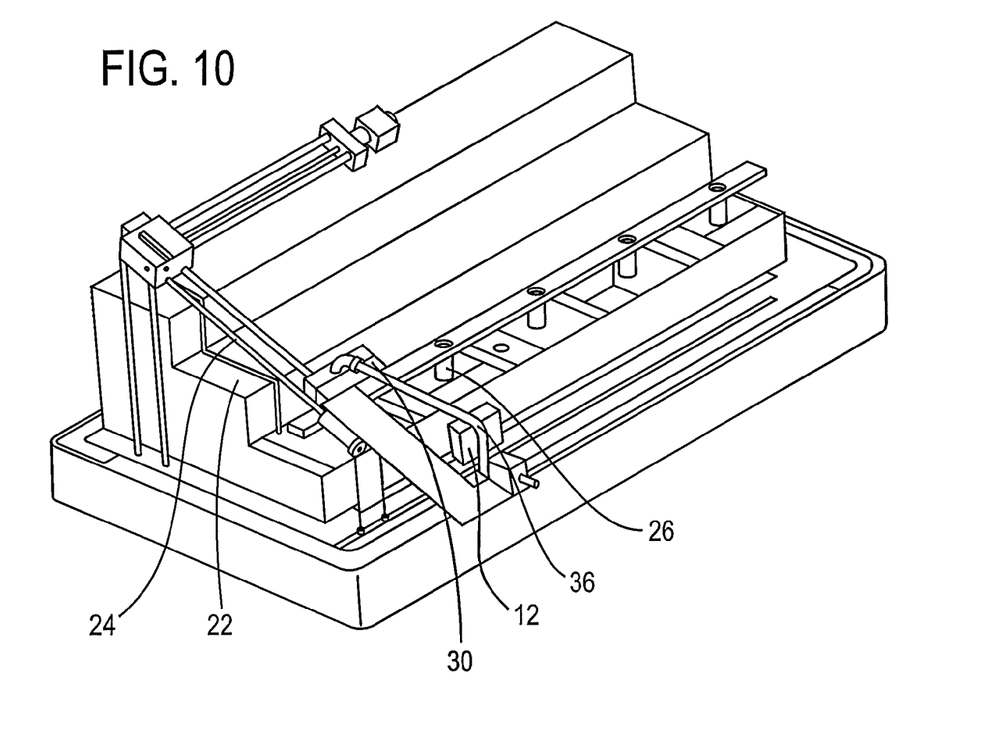
FIG. 10 shows a perspective view of the automated bubble detection apparatus including the support surfaces of FIG. 9.

In another embodiment, as shown in FIGS. 9 and 10, the apparatus 5 can include one or more horizontal support surfaces 22 spaced vertically such as in a stair-step arrangement, each holding one or more test coupons 14. In this embodiment, the carriage 24 can be arranged such that the carriage moves horizontally, vertically and diagonally to position the camera 12 (shown in FIG. 10) in front of each tube 26. As in other embodiments, it is preferred that a light 30 be positioned opposite the camera 12 such that each tube 26 is between the camera 12 and light 30 when recording video segments. Also preferably, the camera 12 is mounted on the carriage 24 via a mounting clamp 36.

Figure 11:
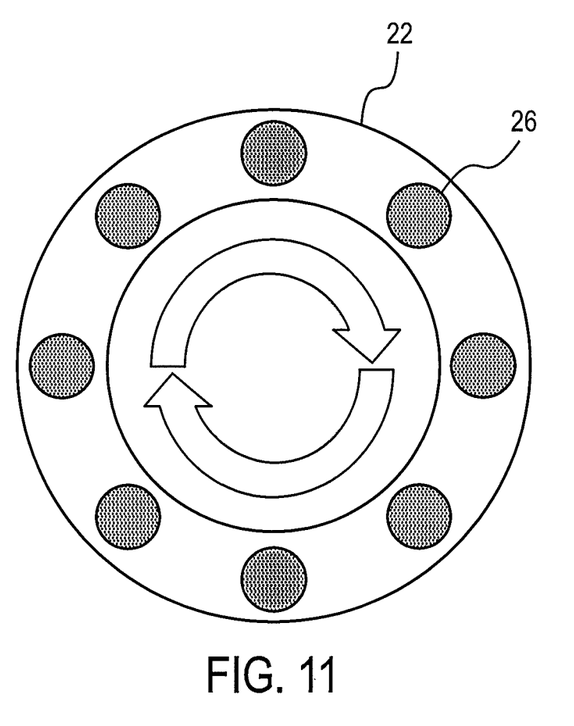
FIG. 11 is an illustration of a third embodiment of a support surface in an annular arrangement.
Figure 12:
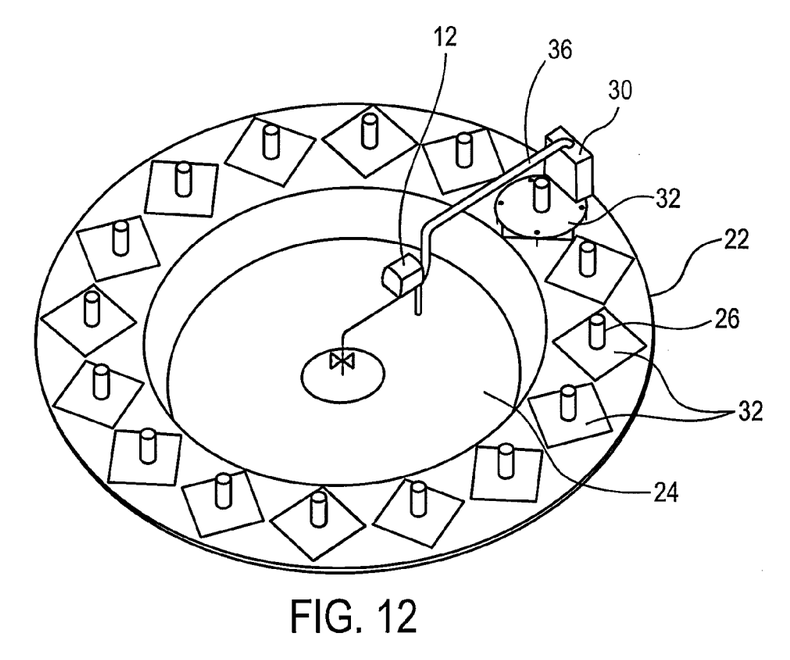
FIG. 12 is a perspective view of the automated bubble detection apparatus including a single support surface having an annular arrangement as shown in FIG. 11.

In yet another embodiment, the support surface 22 can be arranged in an annular configuration as shown in FIGS. 11 and 12. The annular support surface 22 can rotate clockwise or counter-clockwise around a stationary camera (not shown). Alternatively, the camera can be positioned on a movable carriage 24 which rotates in a clockwise or counter-clockwise fashion around or within the annular support surface 22. As in other embodiments, it is preferred that a light 30 be positioned opposite the camera 12 such that each tube 26 is positioned between the camera 12 and light 30 when recording video segments, as shown in FIGS. 12 and 13.

Figure 13:
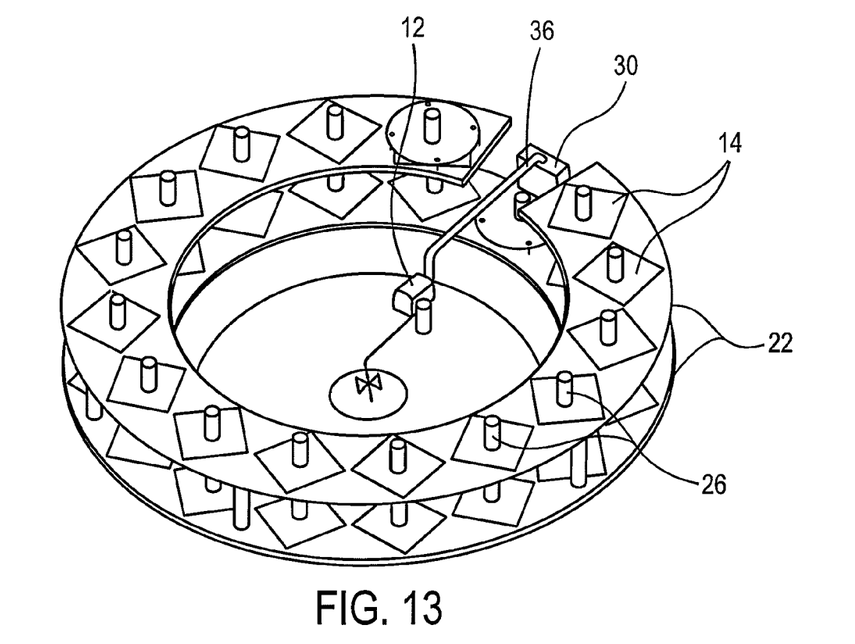
FIG. 13 is a perspective view of the automated bubble detection apparatus including multiple support surfaces having an annular arrangement as shown in FIG. 11.

In one embodiment, the apparatus 5 can include two or more vertically spaced annular support surfaces 22 as shown in FIG. 13. Each annular support surface 22 can hold multiple test coupons.

Preferably, a clamping arrangement 32 clamps the tube 26 to the exposed surface of each test coupon 14. As shown, the upper support surface 22 can be discontinuous so as to allow passage of the mounting clamp 36 holding the light 30 therethrough so that the camera 12 and light 30 can be positioned adjacent each of the test coupons 14 held on the lower annular support surface 22.

Figure 16:
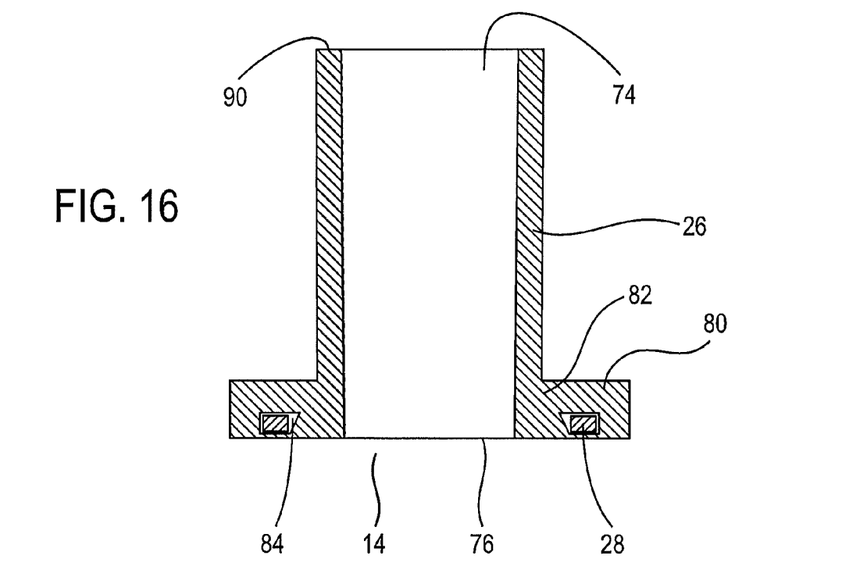
FIG. 16 is a cross-sectional view of a tube and o-ring for sealing the tube to the test coupon as shown in FIGS. 14 and 15.

In each embodiment, the tube 26 preferably comprises transparent polymer, quartz or glass material. The tube 26 can have an open top 74 and an open bottom 76 as shown in FIG. 16, and can have a generally circular cross-section. Alternatively, the tube 26 can have a generally polygonal cross-section. Preferably, the tube is about 1 inch to about 2 inches in height, has an inner diameter of about 0.5 inch to about 1.5 inch and an outer diameter of about 0.6 inch to about 1.75 inch. Thus, the wall of the tube 26 has a thickness of about 0.1 inch to about 0.25 inch. For example, the tube 26 can have an inner diameter of about 0.8 inch and an outer diameter of about 1.0 inch. Also preferably, the diameter of the tube is substantially uniform along the length thereof. Preferably, the thickness of the wall of the tube 26 is selected to provide sufficient strength and the diameter is selected to hold a sufficient quantity of test solution. Also preferably, the tube holds about 20 milliliters (ml) to about 150 ml of test solution (e.g., about 20 ml to about 40 ml, about 40 ml to about 60 ml, about 60 ml to about 80 ml, about 80 ml to about 100 ml, about 100 ml to about 120 ml, about 120 ml to about 150 ml). Also preferably, the open bottom of the tube 26 covers about 2 $mm^2$ to about 20 $mm^2$ of the test coupon (e.g., about 2 $mm^2$ to about 4 $mm^2$, about 4 $mm^2$ to about 6 $mm^2$, about 6 $mm^2$ to about 8 $mm^2$, about 8 $mm^2$ to about 10 $mm^2$, about 10 $mm^2$ to about 12 $mm^2$, about 12 $mm^2$ to about 14 $mm^2$, about 14 $mm^2$ to about 16 $mm^2$, about 16 $mm^2$ to about 18 $mm^2$, or about 18 $mm^2$ to about 20 $mm^2$).

Preferably, the tube 26 is mounted to the surface 15 of the test coupon 14 using a clamping arrangement 32 and sealed to the surface 15 using an O-ring 28 as shown in FIGS. 14, 15, 16, 17 and 18. Alternatively, the tube 26 can be affixed to the surface 15 of the test coupon 14 using a clamping arrangement 32 and an epoxy.

Figure 14:
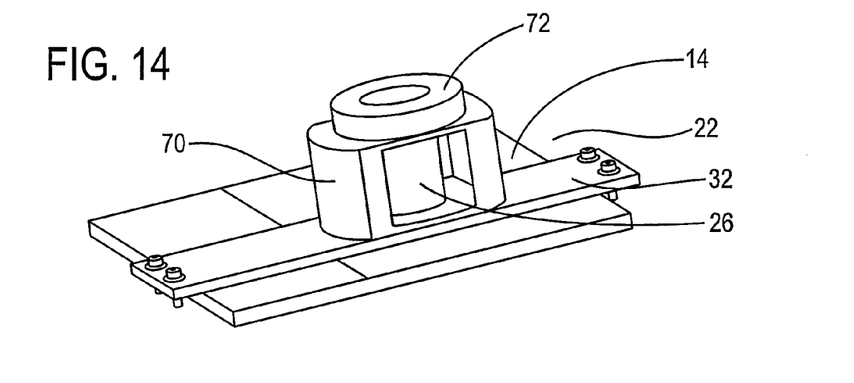
FIG. 14 is a perspective view showing a clamping and sealing arrangement for mounting a tube to a test coupon.
Figure 15:
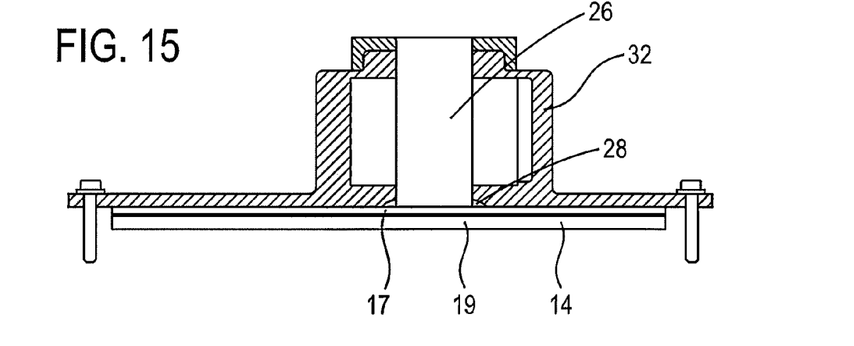
FIG. 15 is a cross-sectional view showing the clamping and sealing arrangement for mounting the tube to the test coupon as shown in FIG. 14.

As shown in FIGS. 14 and 15, a clamping arrangement 32 is provided to clamp the tube 26 in place. The clamping arrangement can span the length of the test coupon 14 and be bolted to the support surface 22 to hold the tube 26 securely against the test coupon 14. The clamping arrangement 32 can include a tubular support member 70 and a disk-shaped member 72, which can be adapted to overlie a top edge 90 (shown in FIG. 18) of the tube 26. An O-ring 28, shown in FIGS. 15 and 16, is included to seal the open bottom 76 of the tube 26 to the surface 15 of the test coupon 14 to prevent leaking of the test solution (e.g., HCl solution) used for testing. In use, the clamping arrangement 32 is clamped such that the tubular support member 70 surrounds the tube, the disk-shaped member 72 overlies the top edge 90 and the clamping arrangement is fastened to the horizontal support surface 22 so as to put downward pressure on the tube 26 and form the seal between the O-ring 28 and the surface 15 of the test coupon 14.

Figure 17:
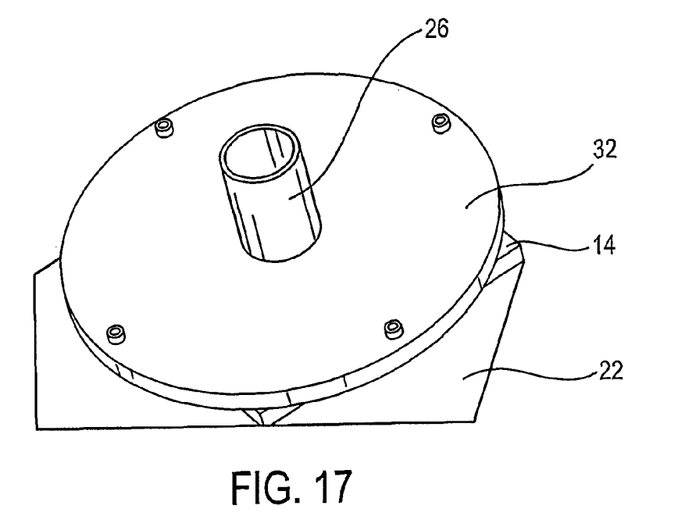
FIG. 17 is a perspective view of a second embodiment of a clamping and sealing arrangement.
Figure 18:
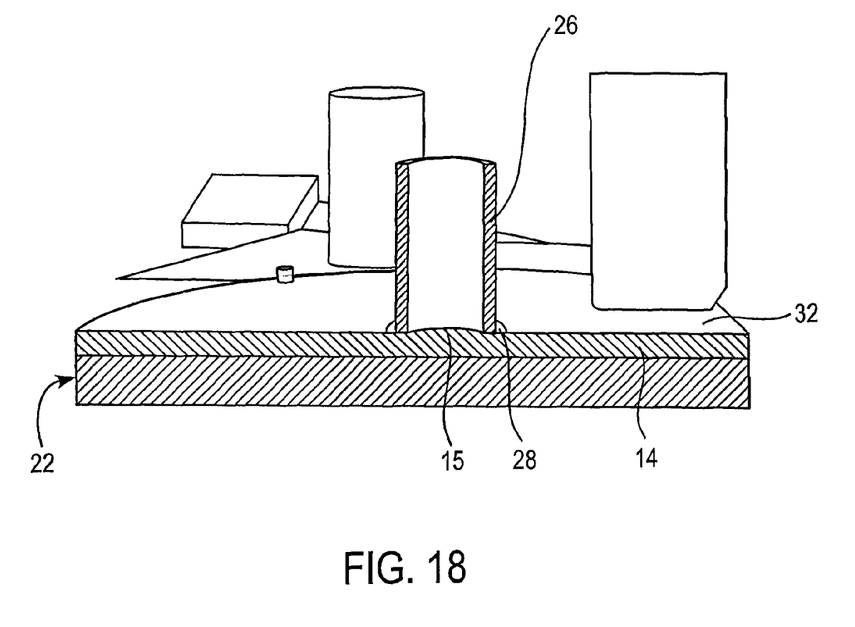
FIG. 18 is a cross-sectional view of the second embodiment of the clamping and sealing arrangement as shown in FIG. 17.

An alternative clamping arrangement 32 is shown in FIG. 17. The clamping arrangement 32 can completely surround the tube 26 and overlie the test coupon 14 as shown. Moreover, the tube 26 can include an annular flange 80 (shown in FIG. 16) extending from the bottom edge 82 of the tube 26. The annular flange 80 can be about 0.1 to about 0.5 inch in height. An annular groove 84 can be formed in the annular flange 80, and the O-ring 28 can be positioned therein. The groove 84 can be substantially rectangular or square in cross-section or can include at least one angled wall. The clamping arrangement 32 overlies the annular flange 80 and puts pressure thereon to form a seal between the O-ring 28 and the surface 15 of the test coupon 14 so as to prevent leaking of the HCl solution during testing.

Once the video segments are recorded, the video segments can be uploaded to the controller 10. A bubble detection algorithm can then be run to detect bubble generation and determine time and date of generation of first bubbles and time to reach steady state bubble generation.

First, image digitization occurs. Image digitization can be based on various criteria. In one embodiment, absolute threshold detection is used to digitize the pixel values of the video segments with black having a pixel value of 0 and white having a pixel value of 255. 8-bit depth video segments are used by the digitization criteria. Alternatively, relative difference detection can be used, which may be more stable than the absolute threshold method. During relative difference detection, if the value of pixels in three previous frames are each greater than the current frame pixel plus a threshold value of 10, then a bubble is suspected to have moved through and the position of that pixel is marked in a vector. The vector is then used to draw black pixels on a white background which becomes the processed image showing the detected bubbles.

After digitization, clustering occurs. Groups are formed from scattered black pixels on the processed images by locating pixels that are connected to each other in a single frame. Then density detection or K-mean clustering can be used. Artificial assumptions can be made at this point and a number of candidate points can be selected from the frame. The connected pixels are clusters, which are considered to be bubbles. A circle can be drawn around each cluster and the clusters can be counted frame by frame to find the bubble count for each image.

Finally, gradient inspection occurs. During this process, the closest two positions, one from the previous frame and a second from the current frame are connected. The vector is the gradient of a certain spot. Only uprising spots are considered bubbles. Spots that do not move vertically from frame to frame are removed from consideration as bubbles.

This information gathered is then used to determine the times for first bubbles and the steady state. The first bubbles are determined by showing at least one bubble passing through two seconds worth of frames. Multiple bubbles may occur at once and still be considered first bubbles. The time of the first bubbles is also noted and can be included in a report generated by the controller.

This information is also used to determine the steady state and time thereof. When 30% of the frame has clusters, which are determined to be bubbles the steady state is determined and flagged. The controller can then stop monitoring of that sample if the analysis is run concurrent with the bubble test. The steady state can also be included in a report generated by the controller.

Figure 19:
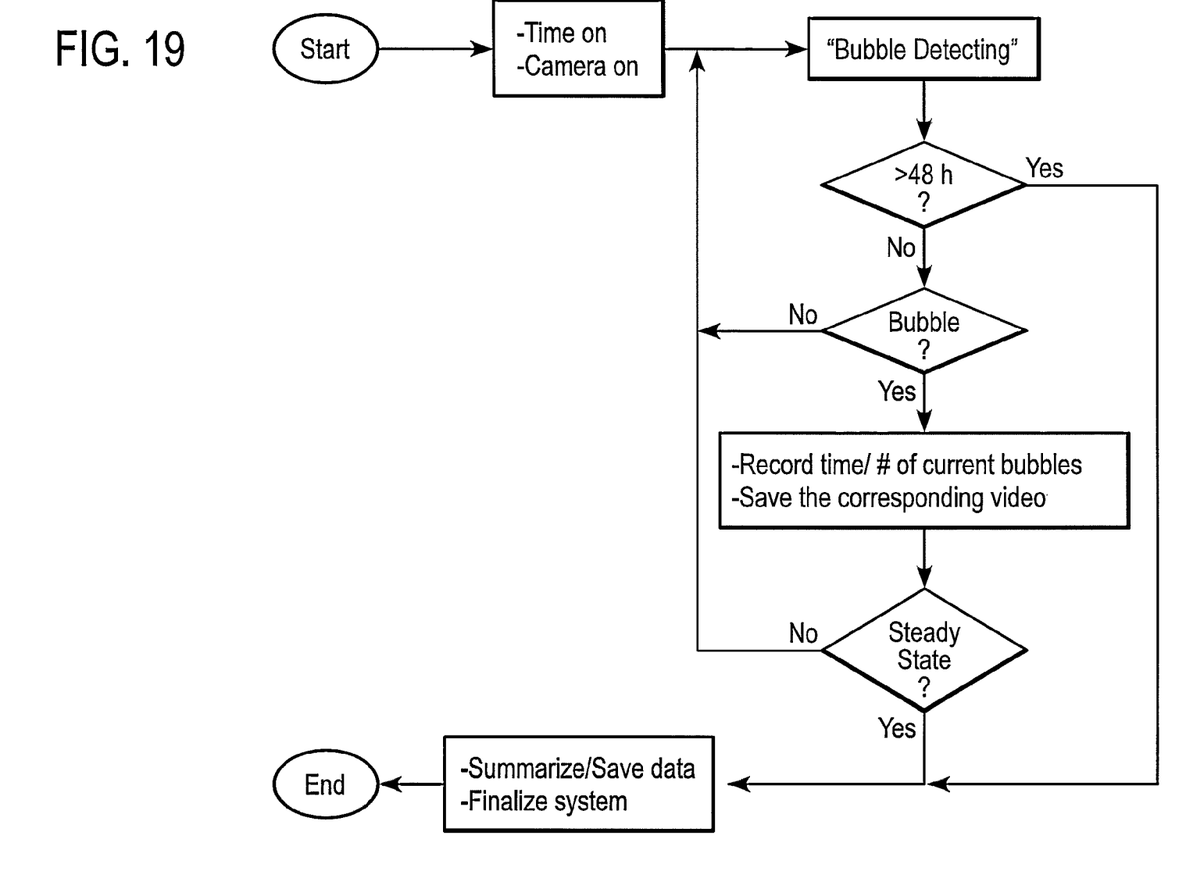
FIG. 19 is a flow chart showing the process for automated hydrogen bubble detection as described herein.

In use, as shown in FIG. 19, once the apparatus is set up and test coupons are in place, the bubble test can begin. At this time, the controller records the start time and the camera is turned on to bubble detection mode. If the test has been run for greater than about 48 hours without detecting first bubbles or steady state, the controller summarizes and saves the data and the test is ended. If the test has been run for less than 48 hours, and bubbles are detected, the time, number of bubbles and video segments are saved by the controller. The controller can then analyze the data to determine the times of first bubbles and steady state as described above. The data can then be summarized and saved. Alternatively, if the test has been run for less than 48 hours and no bubbles have been detected, the apparatus stays in bubble detection mode until either the end of 48 hours or until bubbles are detected.

In this specification, the word "about" is often used in connection with numerical values to indicate that mathematical precision of such values is not intended. Accordingly, it is intended that where "about" is used with a numerical value, a tolerance of 10% is contemplated for that numerical value.

While the foregoing describes in detail an automated hydrogen bubble detection apparatus and method with reference to a specific embodiment thereof, it will be apparent to one skilled in the art that various changes and modifications equivalents to the automated hydrogen bubble detection apparatus and process steps may be employed, which do not materially depart from the spirit and scope of the invention.

We claim:

1. An automated bubble detection apparatus comprising:
    a horizontal support surface on which a test coupon having a coating to be evaluated for its corrosion resistance is supported;
    a transparent tube containing an acidic test solution positioned on the test coupon;
    a camera arranged to view and record video segments of the test solution in the transparent tube; and
    a controller in communication with the camera and effective to operate the camera such that the video segments are recorded at timed intervals and the recorded images are analyzed for presence of bubbles in the test solution;
    wherein
    (a) the automated bubble detection apparatus includes two or more transparent tubes each mounted to different test coupons supported on the horizontal support surface and
    (b) each tube has an inner diameter ranging from about 0.5 inch to about 1.5 inch and an outer diameter ranging from about 0.6 inch to about 1.75 inch;
    a plurality of test coupons are supported on the at least one horizontal support surface;
    transparent tubes containing an acidic test solution are positioned on each test coupon;
    the horizontal support surface is an annular surface and the annular surface is rotatable around the camera; and
    the test coupon includes a ceramic coating over an anodized layer of aluminum.

2. The automated bubble detection apparatus of claim 1, wherein (a) the transparent tube is positioned between the camera and a light and (b) the light is a blue LED light.

3. An automated bubble detection apparatus comprising:
    a horizontal support surface on which a test coupon having a coating to be evaluated for its corrosion resistance is supported;
    a transparent tube containing an acidic test solution positioned on the test coupon;
    a camera arranged to view and record video segments of the test solution in the transparent tube; and
    a controller in communication with the camera and effective to operate the camera such that the video segments are recorded at timed intervals and the recorded images are analyzed for presence of bubbles in the test solution;
    wherein
    (a) the automated bubble detection apparatus includes two or more transparent tubes each mounted to different test coupons supported on the horizontal support surface and (b) each tube has an inner diameter ranging from about 0.5 inch to about 1.5 inch and an outer diameter ranging from about 0.6 inch to about 1.75 inch;

the camera is mounted on a movable carriage which sequentially positions the camera adjacent the transparent tubes at predetermined intervals of time; and the test coupon includes a ceramic coating over an anodized layer of aluminum.

4. The automated bubble detection apparatus of claim 1, wherein (a) the camera records data for up to about 48 hours, (b) the camera is a monochrome camera having a resolution of at least about 1240×1080 pixels and a frame rate of at least about 35 fps and (c) the camera is positioned about 8 inches to about 12 inches from the transparent tube.

5. The automated bubble detection apparatus of claim 1, wherein the test solution is a 2 wt. % to a 5 wt. % HCl solution, a 2 wt. % to a 5 wt. % $HNO_3$ solution or a 2 wt. % to a 5 wt. % $H_2SO_4$ solution and the test solution reacts with a metal layer of a test coupon to form $H_2$ bubbles.

6. The automated bubble detection apparatus of claim 1, wherein the automated bubble detection apparatus includes at least two horizontal support surfaces arranged side by side or spaced vertically; and the test coupons are supported on the horizontal support surfaces.

7. The automated bubble detection apparatus of claim 1, wherein the transparent tube is sealed to a test coupon by an O-ring or an epoxy.

8. The automated bubble detection apparatus of claim 1, wherein (a) the controller comprises a computer and (b) the controller includes a memory which can be programmed to include sub-folders and the video segments can be uploaded corresponding sub-folders for analysis.

9. A method of detecting corrosion resistance of coatings on aluminum and steel exposed to an acidic solution comprising:

mounting a transparent tube having an open top and an open bottom on a test coupon supported on a horizontal support surface such that an open bottom of the tube is sealed to an exposed surface of the test coupon;

placing a quantity of an acidic test solution in the transparent tube such that the acidic test solution contacts a surface of the test coupon;

positioning a camera adjacent the transparent tube such that the acidic test solution is in the field of view of the camera;

recording video segments of the acidic test solution in the transparent tube over a period of time;

uploading the video segments from the camera to a controller; and analyzing the video segments uploaded to the controller to determine first bubbles and steady state bubble generation;

wherein the method includes mounting two or more additional transparent tubes on two or more additional test coupons, placing acidic test solution in the additional transparent tubes and recording video segments of the acidic test solution in the additional transparent tubes, where each tube has an inner diameter ranging from about 0.5 inch to about 1.5 inch and an outer diameter ranging from about 0.6 inch to about 1.75 inch;

the camera is mounted on a movable carriage which sequentially positions the camera adjacent the transparent tubes at predetermined intervals of time, or the horizontal support surface is an annular surface and the annular surface is rotatable around the camera; and the test coupon includes a ceramic coating over an anodized layer of aluminum.

10. The method of claim 9, wherein the test solution is a 2 wt. % to a 5 wt. % HCl solution, a 2 wt. % to a 5 wt. % $HNO_3$ solution or a 2 wt. % to a 5 wt. % $H_2SO_4$ solution and the controller analyzes video segment images for generation of $H_2$ bubbles.

11. The method of claim 9, wherein the camera periodically records video segments of the at least one tube for up to about 48 hours.

12. The method of claim 9, wherein (a) the analyzing includes running a detection algorithm against the video segments to detect the first bubbles generation and the steady state bubble generation and (b) the analyzing includes converting each video segment to a binary image and analyzing the image to identify clusters of bubbles in each video segment.

13. The method of claim 9, further including (a) positioning the camera adjacent each transparent tube every three to five minutes so as to record one or more video segments of each transparent tube or (b) sequentially positioning each of the two or more transparent tubes adjacent the camera every three to five minutes.

14. The method of claim 9, wherein (a) the transparent tube is positioned between the camera and a light, and (b) the light is a blue LED light.

* * * * *